United States Patent
Doppelt

(12) 
(10) Patent No.: US 7,238,820 B2
(45) Date of Patent: Jul. 3, 2007

(54) FLUORINE-FREE METALLIC COMPLEXES FOR GAS-PHASE CHEMICAL METAL DEPOSITION

(75) Inventor: Pascal Doppelt, Noisy-le-Sec (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 10/529,569

(22) PCT Filed: Sep. 25, 2003

(86) PCT No.: PCT/FR03/02820

§ 371 (c)(1),
(2), (4) Date: Sep. 29, 2005

(87) PCT Pub. No.: WO2004/029061

PCT Pub. Date: Apr. 8, 2004

(65) Prior Publication Data

US 2006/0121709 A1    Jun. 8, 2006

(30) Foreign Application Priority Data

Sep. 30, 2002 (FR) .................................. 02 12059

(51) Int. Cl.
*C07C 49/92* (2006.01)
*C07F 1/00* (2006.01)
*C23C 16/00* (2006.01)
(52) U.S. Cl. ...................... 556/40; 556/113; 427/248.1
(58) Field of Classification Search .................. 556/40, 556/113; 427/248.1
See application file for complete search history.

(56) References Cited

U.S. PATENT DOCUMENTS 5,085,731 A     2/1992  Norman et al.
6,838,573 B1 *  1/2005  Farnia et al. .................. 556/41

* cited by examiner

*Primary Examiner*—Shaojia Anna Jiang
*Assistant Examiner*—MLouisa Lao
(74) *Attorney, Agent, or Firm*—Alston & Bird LLP

(57) ABSTRACT

The invention concerns novel copper or silver complexes and their use for gas-phase chemical deposition of metal copper or silver almost free of impurities.

13 Claims, 1 Drawing Sheet

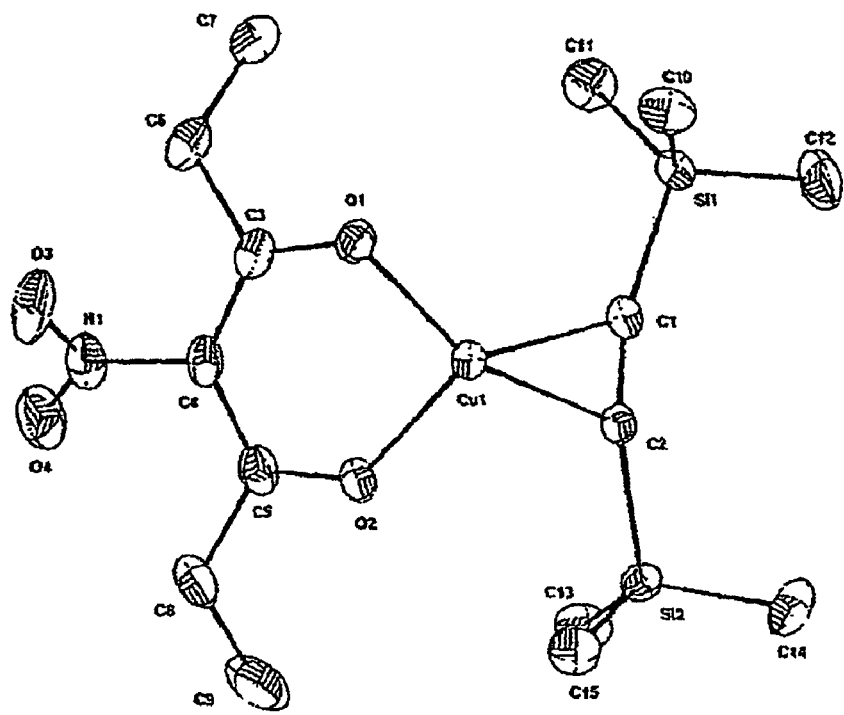
Figure 1: Molecular structure of the (4-NO$_2$-3,5-heptanedionato)Cu(BTMSA) complex obtained by single-crystal X-ray diffraction.

FLUORINE-FREE METALLIC COMPLEXES FOR GAS-PHASE CHEMICAL METAL DEPOSITION

The invention relates to novel copper (I) or silver (I) complexes and to their use for the gas-phase chemical deposition of metal copper or silver virtually free of impurities.

The electronics industry produces integrated circuits for which the requirement in terms of miniaturization, of rapidity and of information storage capacity is ever increasing. The production of metal films for producing the metal interconnections in the integrated circuits via a process of vapor-phase metal deposition is well known to those skilled in the art. Such a process is generally referred to as CVD "Chemical Vapor Deposition". This method uses precursors of these metals in the (+1) oxidation state as starting products.

Many copper precursors are known in the prior art for developing films consisting of pure copper. The most promising precursors are coordination complexes of copper in the (+1) oxidation state stabilized by means of a ligand, in which the copper is coordinated with a β-diketonate, corresponding to general formula (I) below:

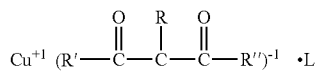

in which R, R' and R", which may be identical or different, are chosen from a hydrogen atom, a halogen atom such as fluorine, and a $C_1$-$C_8$ alkyl group optionally substituted with one or more fluorine atoms.

Preferred complexes are those in which R is a hydrogen atom and R' and R" are perfluoro alkyls and advantageously —$CF_3$ groups corresponding to the structural formula below:

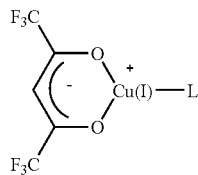

Such complexes and their use for CVD are described, for example, in U.S. Pat. Nos. 5,085,731, 5,096,737, 5,098,516, 5,144,049 and 5,187,300, and in International Application Ser. No. 98/40387.

Studies carried out on these precursors show that their molecular structure is decisive for the reproducible production of films of good quality (P. Doppelt and T. H. Baum, MRS Bull. XIX(8), 41, 1994, T. Y. Chen, J. Vaissermann, E. Ruiz, J. P. Senateur, P. Doppelt, *Chem. Mat.* 13, 3993 (2001)).

As has been described in the abovementioned patents, the formation of the metal copper is the result of dismutation of two molecules of copper (1) on a surface heated to a temperature in the region of 200° C., according to the following reaction scheme:

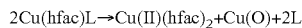

in which hfac represents the hexafluoroacetyl-acetonate anion and L represents the Lewis base or Ligand. The mechanism is the same for the other copper (I) complexes and for silver (I) complexes.

The nature of the Lewis base L, also referred to hereinafter as a ligand, has very little influence on the nature of the copper films obtained by CVD. The copper films are generally very pure, and in particular free of carbon atoms, oxygen atoms and fluorine atoms (less than 1%). A resistivity of the order of 1.8 μΩ.cm is commonly found in the copper films obtained by CVD; this value is very close to that found in bulk copper (1.67 μΩ.cm).

On the other hand, the nature of the ligand L determines the volatility of the complex and, consequently, the rate of copper deposition.

In the documents of the prior art, in particular in U.S. Pat. Nos. 5,098,516 and 5,144,049, preference is generally given to complexes of copper (I) and of anions bearing fluorine atoms, in particular due to their volatility, which makes it possible to carry out the metal deposition at temperatures that are lower than when the anion is not a fluorinated molecule, and also because of the greater stability of these complexes.

The technology provided for the copper metallization of electronic components requires that the copper be deposited on a barrier film that prevents the copper from diffusing in the dielectric and allows the integrity of the electrical contact.

This barrier is chosen from materials such as TiN, TaN or WN (titanium nitride, tantalum nitride and tungsten nitride, respectively) or metal Ta. Other materials may optionally be used.

Now, in certain cases, in particular when the copper film is deposited on TiN, Ta or TaN, as required by the technology, even though the copper film contains only a very small amount of fluorine, this fluorine diffuses and becomes concentrated at the interface between the copper and the barrier.

This phenomenon has been described in particular by K. Weiss, S. Riedel, S. E. Schultz, T. Gessner, *AMC* 1998, *MRS Proceedings* page 171.

The result of this is:
1) a break in the electrical conductivity between the base transistor and the copper film, which increases, overall, the resistivity of the contact, due to the insulating nature of the fluorine-rich film;
2) insufficient adhesion of the copper film on the barrier film.

The compounds described in document WO 98/40387 provided a first response to this problem.

However, there remains a need for a copper (I) or silver (I) complex for the reproducible production of electronic circuits based on thin copper or silver films for filling vertical interconnections and lines without fault and with low resistivity and good thermal stability in the long term.

In particular there remains a need for a precursor which is completely free of fluorine atoms, while at the same time being volatile and sufficiently stable to be exploited industrially.

Finally, this precursor must decompose thermally according to the dismutation reaction given above, so as to ensure that the metal film deposited is highly pure.

The applicant has developed novel compounds, which are fluorine-free copper (I) or silver (I) complexes that are precursors of copper or of silver in the gas-phase metal deposition process, these compounds remedying the drawbacks of the prior art.

The compounds according to the invention are characterized in that they correspond to formula (I) below:

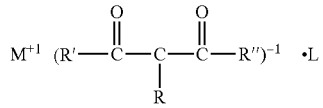

in which

M represents a copper atom or silver atom;

R' and R", which may be identical or different, represent a group chosen from: a $C_1$-$C_8$ alkyl; an —OR''' group, in which R''' represents a $C_1$-$C_8$ alkyl;

R represents a group chosen from: an —OR'''' group, in which R'''' represents a $C_1$-$C_8$ alkyl; a nitro group: $NO_2$; an aldehyde function: —CHO; a —COOR'''' ester function, in which R'''' represents a $C_1$-$C_8$ alkyl group;

L represents the ligand for stabilizing this complex.

L may be chosen from the ligands used in the prior art as stabilizers of copper (I) complexes, in particular the ligands described in the documents already mentioned above.

Among the ligands that can be used in the present invention, mention may be made of:

a—carbon monoxide, b—unsaturated hydrocarbon-based ligands containing at least one nonaromatic unsaturation, and in particular among the latter: ethylene, acetylene, 1-octene, isobutylene, 1,5-cyclooctadiene, stilbene, diphenylacetylene, styrene, cyclooctene, 1,5,9-cyclo-dodecatriene, 1,3-hexadiene, isopropylacetylene, 1-decene, 2,5-bicycloheptadiene, 1-octadecene, cyclo-pentene, octaline, methylene cyclohexane, diphenylfulvene, 1-octadecyne, benzylcinnamate, benzal acetophenone, acrylonitrile, maleic anhydride, oleic acid, linoleic acid, acrylic acid, methyl methacrylate, diethyl maleate, methyl-1,5-cyclooctadiene, dimethyl-1,5-cyclooctadiene, methylcyclooctene, cycloocta-tetraene, norborene, norboradiene, tricyclo[5.2.1.0]-deca-2,6-diene, 1,4-cyclohexadiene or [4,3,0]bicyclo-nona-3,7-diene;

c—isonitriles such as in particular methyl isocyanide, butyl isocyanide, cyclohexyl isocyanide, phenylethyl isocyanide, phenyl isocyanide;

d—phosphines such as, for example, trimethyl-phosphine or triethylphosphine, e—the compounds corresponding to formula (II) below:

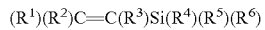

in which $R^1$ represents the hydrogen atom or a $C_1$-$C_8$ alkyl group or an $SiR^4R^5R^6$ group, $R^2$ and $R^3$, which may be identical or different, represent the hydrogen atom or a $C_1$-$C_8$ alkyl group, $R^4$, $R^5$ and $R^6$, which may be identical or different, represent a phenyl or $C_1$-$C_8$ alkyl group;

f—the compounds corresponding to formula (III) below:

in which $R^7$ represents a $C_1$-$C_8$ alkyl, phenyl or $Si(R^8)(R^9)(R^{10})$ group, $R^8$, $R^9$ and $R^{10}$, which may be identical or different, represent a $C_1$-$C_8$ alkyl or phenyl group, g—the compounds corresponding to one of the formulae (IV), (V) and (VI) below:

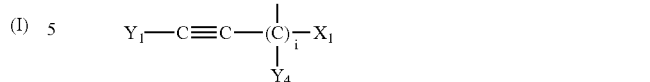

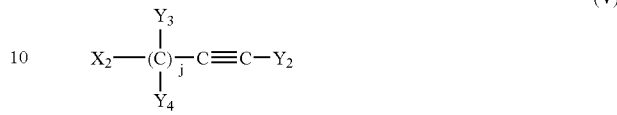

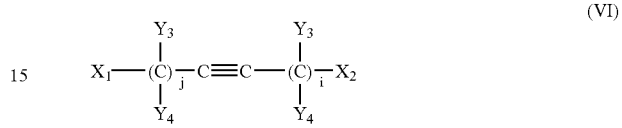

in which $Y_1$, $Y_2$, $Y_3$ and $Y_4$, which may be identical or different, are chosen from a hydrogen atom, a $C_1$-$C_8$ alkyl and an —$Si(R_5)_3$ group where $R_5$ is a $C_1$-$C_8$ alkyl, i and j represent an integer chosen from 0, 1, 2 and 3, and $X_1$ and $X_2$, which may be identical or different, represent an electron-withdrawing group, such as in particular a $C_1$-$C_8$ alkenyl; examples of products corresponding to formulae (IV), (V) and (VI) are illustrated in international application WO 98/40387.

For the purpose of the present invention, the term "alkyl" denotes linear, branched or cyclic hydrocarbon-based radicals. It is understood in particular that two alkyl radicals of the same molecule may be attached to form a cyclic molecule.

The preferred molecules of the present invention are those corresponding to formula (I) for which one or more of the conditions below is (are) satisfied:

M represents the copper atom,

R' or R" represent a group chosen from $CH_3$ and $C_2H_5$,

R represents a group chosen from $NO_2$ and $OCH_3$,

L represents a ligand chosen from 1,5-cyclooctadiene and bis(trimethylsilyl)acetylene.

The compounds of the present invention can be prepared by means of a process already described in the prior art: P. Doppelt, T. H. Baum, L. Richard, *Inorg. Chem.* 35, 1286, 1996.

A subject of the invention is also a process for the gas-phase chemical deposition of a metal chosen from copper and silver, on a support. The support may consist of a material chosen in particular from Si, AsGa, InP, SiC and SiGe. The copper layer can be deposited on said support as a first metallization layer or as an $n^{th}$ metallization layer for electronic devices requiring several levels of metallization, n being an integer greater than or equal to 2. The support may consist of one of the abovementioned materials taken as it is, or else of one of these materials bearing one or more intermediate layers. By way of example of intermediate layers, mention may be made of diffusion layers consisting of at least one material chosen, for example, from TiN, TiSiN, Ta, TaN, TaSiN, WN and WSiN. The process according to the invention consists in applying a gas-phase chemical deposition, or CVD, process already known from the prior art to the copper precursor and silver precursor compounds described above.

This process makes it possible in particular to make a selective deposit of the chosen metal on the electrically conducting surface of the support while at the same time avoiding depositing it on the insulating portions of this same support, such as, for example, the portions made of silicone dioxide of the supports of integrated circuits.

Advantageously, this process is carried out at a temperature ranging from 120 to 300° C.

According to the case, the compound according to the invention is used pure when this compound is a liquid at ambient temperature, or in solution if this compound is solid at ambient temperature.

The solid compounds are advantageously dissolved in a hydrocarbon-based solvent, in particular in a cyclic hydrocarbon-based solvent, such as, for example, cyclohexane or tetrahydrofuran, or aromatic solvents such as toluene, xylene or mesitylene. The compounds according to the invention can be used in standard equipment for CVD, as commonly used in the electronics industry. They have the advantage of not releasing harmful compounds capable of damaging a substrate for an integrated circuit or of decreasing its selectivity.

During the implementation of the process for depositing copper or silver layers on a support, the composition containing the metal precursor is conveyed into a vaporizing device via which it is introduced into the reactor which contains the support on which the copper or silver layer must be deposited. Before it reaches the vaporizing device, the composition is generally kept in a reservoir at ambient temperature. The precursor composition can be vaporized by means of various devices known to those skilled in the art. By way of preferred example, mention may be made of the device described in the document T. Y. Chen, J. Vaissermann, E. Ruiz, J. P. Sénateur, P. Doppelt, *Chem. Mat.* 2001, 13, 3993. Said device, sold by the company Jipelec under the name "TriJet Liquid Precursor Delivery and Evaporation System", comprises three main parts: the reservoir, an injector and an evaporator. The solution of copper (I) complex, which is located in the reservoir kept at a pressure of 1 bar, is propelled, by means of the injector, through a difference in pressure in the evaporator, which is kept under vacuum. The injection flow rate is controlled by a computer-controlled micro-electrovalve. The evaporator and also the rest of the assembly, which consists mainly of a reaction chamber for a single support, are kept at the same temperature.

The thickness of copper that is deposited on the support depends on the concentration of the precursor composition, on the flow rate of this composition when it passes through the vaporizing device, on the duration of the vaporization, and on the respective temperatures in the reactor and on the support. In general, less concentrated compositions and/or lower flow rates are used to obtain thin layers, and more concentrated compositions and/or higher flow rates are used to obtain thick layers. The term "thin layer" is generally intended to mean a layer having a thickness of less than or equal to 50 nm, referred to as nucleating layer. The term "thick layer" is generally intended to mean a layer having a thickness of between 50 nm and 1 μm. The process according to the invention makes it possible to realize, using precursors of metals in the (+1) oxidation state, the interconnections and metallization of integrated circuits with a thickness ranging from 0.2 to 500 nm, preferably from 0.2 to 50 nm.

The use of the compositions according to the invention for developing copper layers by CVD makes it possible to obtain copper layers of good quality that adhere well to the support on which they are deposited.

EXPERIMENTAL SECTION

Abbreviations Used
acac: acetylacetone anion.
COD: 1,5-cyclooctadiene.
BTMSA: bis(trimethylsilyl)acetylene.
EDTA: disodium ethylenediaminetetraacetic acid.
GCMS: Gas Chromatography Mass Spectroscopy
3-$NO_2$-acac: 3-nitroacetylacetone anion.
3-MeO-acac: 3-MeO-acetylacetone anion.

I—Synthesis of Non-fluorinated β-diketones

I-1. Synthesis of 3-$NO_2$-acac

The synthesis of $NO_2$-acac takes place in two stages as described in the literature by Z. Yoshida, H. Ogoshi and T. Tokumitsu, *Tetrahedron,* 1970, 26, 5691. The first stage consists in forming the complex of copper (II): bis-(3-nitro-2,4-pentanediono)-copper (II) (Cu($NO_2$-acac)$_2$, the second in isolating the β-diketone by decomplexation using EDTA.

a—Synthesis of Cu($NO_2$-acac)$_2$

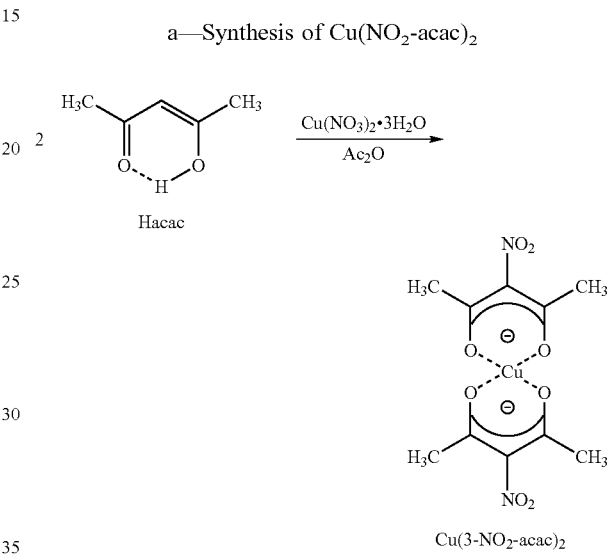

50 ml of acetic anhydride and 10 ml (0.09 mol) of acetyl acetone are introduced into a round-bottomed flask. 7.89 g (33 mmol) of sodium nitrate trihydrate are then added (in several fractions since the reaction is exothermic) with stirring and at 0° C. (water/ice bath). The reaction medium is left, with stirring, for two hours at 0° C. and then eighteen hours at ambient temperature.

The green-colored solution is then treated with a sodium acetate/ice-cold water solution (approximately 100 ml), which gives a green precipitate in suspension, which is filtered through a Büchner funnel and then dried over $P_2O_5$. The yield is 42%.

Melting point: 240° C. (decomp.). IR (cm$^{-1}$): 1586 (γ C=O), 1525 (γ$_{as}$ $NO_2$), 1336 (γ$_s$ $NO_2$). Sublimation at T=100° C. under P=4×10$^{-1}$ mbar.

b—Synthesis of 3-$NO_2$acac

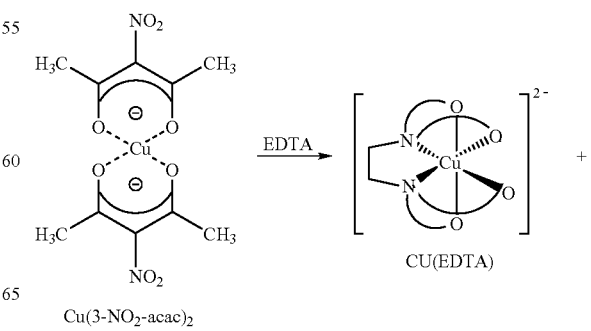

-continued

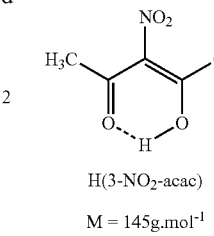

H(3-NO$_2$-acac)

M = 145 g.mol$^{-1}$ 9.3 g (22.8 mmol) of Cu(NO$_2$-acac)$_2$ in suspension in 120 ml of dichloromethane are introduced into a 500 ml round-bottomed flask. 120 ml of water are added and two phases are obtained: the colored organic phase (in which the copper (II) complex dissolves) and the aqueous phase (in which the copper/EDTA complex forms). EDTA is added until a decolorated organic phase is obtained. The organic phase is separated from the aqueous phase by settling out, and dried over MgSO$_4$. The nitrogenous diketone is obtained by evaporation of the solvent and purified by distillation under reduced pressure (P=10$^{-1}$ mbar, T=45° C.). The yield is 77%.

GCMS: 1 peak at m/z=145. NMR (CDCl$_3$, T=297 K): $^1$H δ (ppm): 15.11 (s, 1H, —C—O—H . . . O=C—), 2.50 (s, 6H, 2-CH$_3$). $^{13}$C δ (ppm): 192.4 (s, —C=O), 134.7 (s, =C—NO$_2$), 24.8 (s, —CH$_3$)

I-2. Synthesis of 4-NO$_2$-3,5-heptanedione a—Synthesis of 4-Cu(NO$_2$-3,5-heptanedione)$_2$ The procedure is identical to that for preparing Cu(NO$_2$-acac)$_2$.

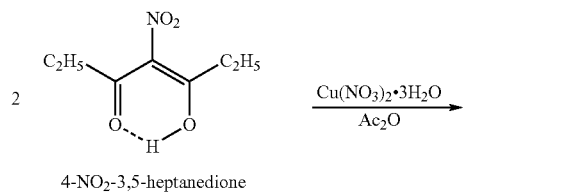

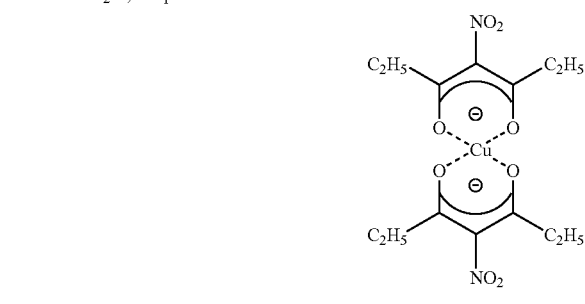

The reaction mixture consists of:
10 g (78 mmol) of 3,5-heptanedione in 50 ml of acetic anhydride,
6.91 g (29 mmol) of sodium nitrate trihydrate.

The product obtained is a dark green solid. The crude yield is 60-65%. The compound can be recrystallized from a hexane/methanol (30 ml/10 ml) mixture.

Melting point: 252° C. IR (cm$^{-1}$): 1582 (γ C=O), 1523 (γ$_{as}$ NO$_2$), 1343 (γ$_s$ NO$_2$). Sublimation at T=120° C. under P=5×10$^{-2}$ mbar.

b—Preparation of 4-NO$_2$-3,5-heptanedione

The procedure is identical to that for preparing 3-NO$_2$-acac:

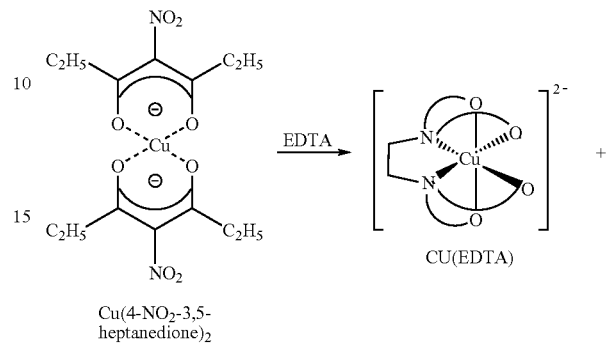

Cu(4-NO$_2$-3,5-heptanedione)$_2$

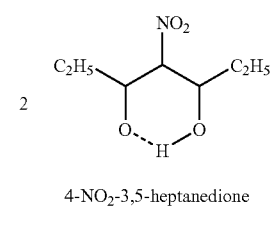

4-NO$_2$-3,5-heptanedione

M = 173 g.mol$^{-1}$

The reaction mixture consists of:
7.72 g (17.7 mmol) of Cu(NO$_2$-3,5-heptane-dione)$_2$,
100 ml of dichloromethane and 100 ml of water,
ETDA.

The diketone is purified by distillation under reduced pressure (P=10$^{-1}$ mbar, T=150° C.). The yield is 58%.

GCMS: 1 single peak for m/z=173. NMR (CDCl$_3$, T=297 K), $^1$H δ (ppm): 15.17 (s, 1H, —C—O—H . . . O=C—), 2.18 (q, 4H, J$^3_{H-H}$=7.35 Hz, 2-CH$_2$), 1.23 (t, 6H, J$^3_{H-H}$=7.35 Hz, 2-CH$_3$), $^{13}$C δ (ppm): 194.9 (s, —C=O), 135.3 (s, =C—NO$_2$), 29.9 (s, —CH$_2$—), 8.9 (s, —CH$_3$)

I-3. Synthesis of 3-MeO-acac

We followed the procedure for preparing this ligand that was described by R. M. Moriarty, R. K. Vaid, V. T. Ravikumar, B. K. Vaid and T. E. Hopkins, *Tetrahedron*, 1988, 44, 1603.

II—Synthesis of the Copper (I) Complexes

For the copper (I) complexes containing the NO$_2$— group or the —OMe group, we chose the synthesis using reaction of the β-diketone on copper (I) oxide in the presence of a Lewis base, as described previously by P. Doppelt, T. H. Baum, *MRS Bulletin,* 1994, XIX(8), 41, since the corresponding β-diketones are sufficiently acidic in nature for the reaction to take place with a good yield. In all cases, it was necessary to work under a controlled atmosphere (under nitrogen).

II-1. Preparation of (3-NO₂-acac)Cu(BTMSA)

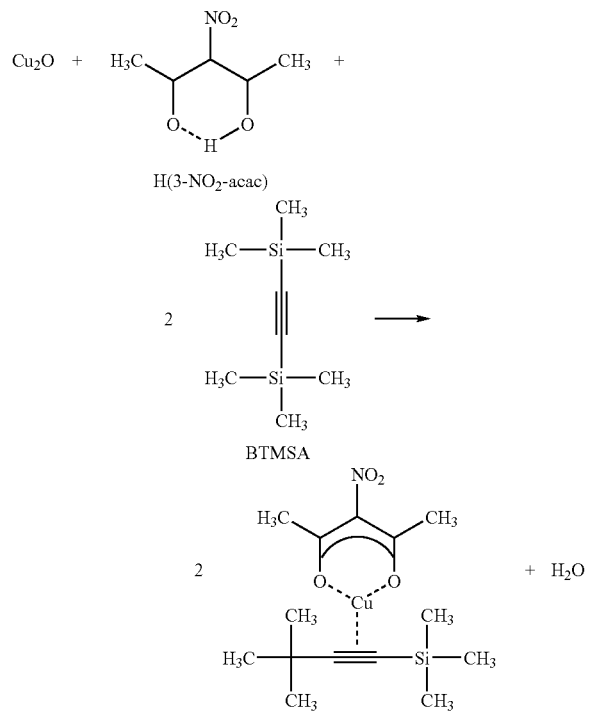

1.03 g (7.22 mmol) of Cu₂O and 1.6 ml (7 mmol) of BTMSA are stirred under a stream of nitrogen in 20 ml of dichloromethane, in a 100 ml round-bottomed flask. 1 g, i.e. 6.9 mmol of 3-NO₂-acac is added dropwise with a syringe. The solution very rapidly becomes yellowish-green in color. The stirring is maintained under N₂ for two hours.

After filtration under nitrogen, the solution is passed through a silica column (inside diameter 3 cm, height 4 cm). After evaporation under vacuum, a yellow solid is obtained. This complex is quite stable in air, but should be stored under nitrogen. The yield is 90%.

Melting point=100° C. IR (cm⁻¹): 1582 (γ C=O), 1511 ($\gamma_{as}$ NO₂), 1349 ($\gamma_s$ NO₂). NMR (CDCl₃, T=297 K) ¹H δ (ppm): 2.26 (s, 6H, 2-CH₃ from NO₂-acac), 0.31 (s, 18 H, 6-CH₃ from BTMSA) ¹³C δ (ppm): 189.0 (s, —C=O), 139.0 (s, =C—NO₂), 27.6 (s, —CH₃ on NO₂-acac), 0.0 (s, —CH₃ from BTMSA). Sublimation at T=50° C.-60° C. under P=5×10⁻² mbar.

II-2. Preparation of (3-NO₂-acac)Cu(COD)

The same procedure as for the preparation of (3-NO₂-acac)Cu(BTMSA) is used.

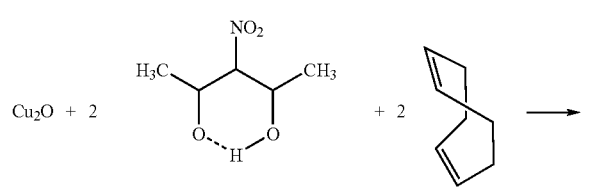

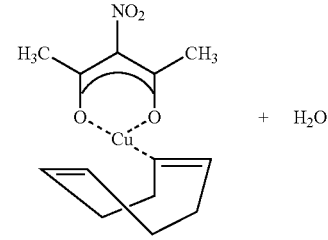

The reaction mixture consists of:
0.83 g (5.79 mmol) of Cu₂O,
0.7 ml (5.64 mmol) of COD,
0.8 g (5.52 mmol) of 3-NO₂-acac,
30 ml of CH₂Cl₂.

The product obtained is a yellow solid. The yield is 60%.
Melting point: 145° C. (decomp.). NMR (CDCl₃, T=297 K) ¹H δ (ppm): 5.46 (s, 4H, 2-HC=CH— from COD), 2.43 (s, 8H, 4-CH₂— from COD), 2.22 (s, 6H, 2-CH₃ from NO₂-acac), ¹³C δ (ppm): 188.4 (s, —C=O), 138.5 (s, =C—NO₂), 114.7 (s, =CH—), 28.0 (s, —CH₂—), 24.9 (s, —CH₃). Sublimation at T=60° C. for P=2×10⁻¹ mbar.

II-3. Preparation of (4-NO₂-3,5-heptane-dionato)Cu(BTMSA)

A procedure identical to that used for the preparation of NO2-acac)Cu(BTMSA) is used

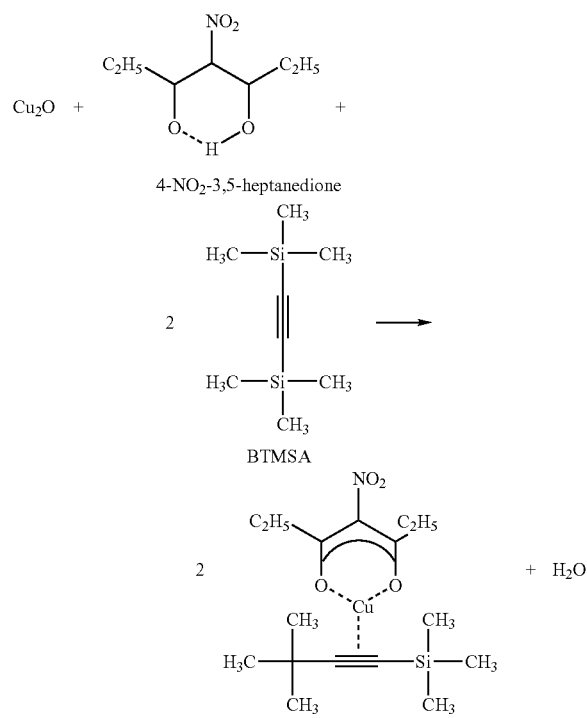

The reaction mixture consists of:
0.598 g (4.18 mmol) of Cu₂O,
0.95 ml (4.08 mmol) of BTMSA,
0.69 g (3.99 mmol) of NO₂-3,5-heptanedione,
20 ml of CH₂Cl₂.

A yellow solid is obtained with a yield of 81%. Its stability is comparable to that of (3-NO$_2$-acac)Cu(BTMSA).

Melting point: 90° C. IR (cm$^{-1}$): 1587 (γ C=O), 1513 (γ$_{as}$ NO$_2$), 1342 (γ$_s$ NO$_2$). NMR (CDCl$_3$, T=297 K) $^1$H δ (ppm): 2.53 (s, 4H, J$^3_{H-H}$=7.35 Hz, 2-CH$_2$— from diketone), 1.12 (t, 6H, J$^3_{H-H}$=7.35 Hz, 2-CH$_3$ from diketone), 0.32 (s, 18H, 6-CH$_3$ from BTMSA), $^{13}$C δ (ppm): 191.2 (s, —C=O), 138.7 (s, =C—NO$_2$), 31.5 (s, —CH$_2$), 10.0 (s, —CH$_3$ on ketone), 0.0 (s, —CH$_3$ on BTMSA). Sublimation at T=60° C. under P=5×10$^{-2}$ mbar.

We succeeded in obtaining monocrystals for this complex, which were used to determine the structure of the complex by X-ray diffraction. This structure is represented in FIG. 1. The structure is very similar to that of the corresponding complexes containing fluorine and which were described by P. Doppelt, T. H. Baum, *J. Organomet. Chem.* 1996, 517, 53. No intermolecular interaction capable of impairing the vaporization of the complex was demonstrated.

II-4. Preparation of (3-MeO-acac)Cu(BTMSA)

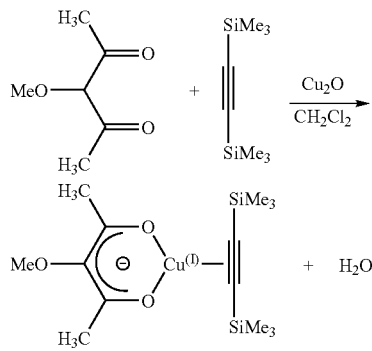

1.6 ml (7 mmol) of BTMSA are added, under nitrogen, to a suspension of Cu$_2$O (1.03 g, 7.22 mmol) in 40 ml of dichloromethane. After 30 minutes, 915 mg (7 mmol) of 3-methoxy-2,4-pentanedione are added dropwise. The solution rapidly becomes orangey-yellow and is left, with stirring, at ambient temperature for 3 hours and filtered using a PTFE cannula. After evaporation of the solvent, an orange residue is obtained. This solid is redissolved in a minimum amount of dichloromethane and passed over a silica column (inside diameter 3 cm, height 4 cm). A white solid is thus obtained.

$^1$H NMR (CDCl$_3$, 300 MHz): 3.45 (s, 3H, O—CH$_3$), 2.05 (s, 6H, 2×C—CH$_3$), 0.2 (s, 18 H, 6×Si—CH$_3$); IR (cm$^{-1}$): 1583 (C=O), 1921 (C≡C).

III. CVD Depositions using Solutions of (4-NO$_2$-3,5-heptanedionato)Cu(BTMSA)

Since the copper complexes described here are solids, they can be used pure in a bubbler, or preferably dissolved in a neutral solvent such as cyclohexane or tetrahydrofuran or aromatic solvents such as toluene, xylene or mesitylene.

The (4-NO$_2$-3,5-heptanedionato)Cu(BTMSA) was tested:

The complex decomposition reaction is the following dismutation reaction:

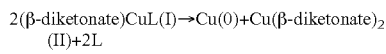

The reaction does not require the action of a reactive gas, the Cu(β-diketonate)$_2$ (II) and L species formed are volatile and evacuated from the system.

We used quite a high concentration of 1 g of complex in 10 g of cyclohexane. Higher concentrations can be used, since the complex is very soluble in most organic solvents. Lower concentrations can be used if the application is rather a copper film as a nucleating layer for electrochemical deposition as indicated above.

Furthermore, in order to increase the stability of the solution, 100 mg of BTMSA were added. This final step is not obligatory and can be eliminated if the product is sufficiently stable.

Using this (4-(NO$_2$-3,5-heptanedionato)Cu(BTMSA) composition, a copper film was deposited on a support kept at 250° C. and placed in a reactor at 100° C. under a pressure of 5 Torr. The (4-NO$_2$-3,5-heptanedionato)Cu(BTMSA) composition is delivered to a vaporizing device at the same time as the nitrogen gas. The flow rate of the nitrogen was 100 sccm (standard cubic centimeter minutes).

In a first trial, the support was a plaque of silicon that had a diameter of 4 inches and that was coated with a film of TiN 200 nm thick, and the precursor composition flow rate was 0.4 ml/min. In a second trial, the support was a plaque of silicon that had a diameter of 8 inches and was coated with a film of TiN 200 nm thick, and the precursor composition flow rate was 2.4 ml/min.

In each case, an adherent copper film of good quality with a growth rate of 1 to 5 nm/min was obtained.

What is claimed is:

1. A compound corresponding to formula (I) below:

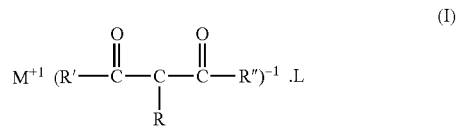

in which
  M represents a copper atom or silver atom;
  R' and R", which may be identical or different, represent a group chosen from: a C$_1$-C$_8$ alkyl; an —OR''' group, in which R''' represents a C$_1$-C$_8$ alkyl;
  R represents a group chosen from: an —OR'''' group, in which R'''' represents a C$_1$-C$_8$ alkyl; a nitro group: NO$_2$; an aldehyde function: —CHO; a —COOR'''' ester function, in which R'''' represents a C$_1$-C$_8$ alkyl group;
  L represents a stabilizing ligand.

2. A compound according to formula (I) of claim 1, wherein L is chosen from:
  a—carbon monoxide,
  b—unsaturated hydrocarbon-based ligands containing at least one nonaromatic unsaturation,
  c—isonitriles,
  d—phosphines,
  e—the compounds corresponding to formula (II) below:

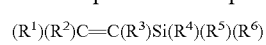

in which
  R$^1$ represents the hydrogen atom or a C$_1$-C$_8$ alkyl group or an SiR$^4$R$^5$R$^6$ group,
  R$^2$ and R$^3$, which may be identical or different, represent the hydrogen atom or a C$_1$-C$_8$ alkyl group,
  R$^4$, R$^5$ and R$^6$, which may be identical or different, represent a phenyl or C$_1$-C$_8$ alkyl group;

f—the compounds corresponding to formula (III) below:

in which
R$^7$ represents a C$_1$-C$_8$ alkyl, phenyl or Si(R$^8$)(R$^9$)(R$^{10}$) group,
R$^8$, R$^9$ and R$^{10}$, which may be identical or different, represent a C$_1$-C$_8$ alkyl or phenyl group, g—the compounds corresponding to one of the formulae (IV), (V) and (VI) below:

in which Y$_1$, Y$_2$, Y$_3$ and Y$_4$, which may be identical or different, are chosen from a hydrogen atom, a C$_1$-C$_8$ alkyl and an —Si(R$_5$)$_3$ group where R$_5$ is a C$_1$-C$_8$ alkyl, i and j represent an integer chosen from 0, 1, 2 and 3, and X$_1$ and X$_2$, which may be identical or different, represent an electron-withdrawing group.

3. A compound as claimed in claim 1, wherein M represents the copper atom.

4. A compound as claimed in claim 1, wherein R' or R" represents a group chosen from CH$_3$ and C$_2$H$_5$.

5. A compound as claimed claim 1, wherein R represents a group chosen from NO$_2$ and OCH$_3$.

6. A compound as claimed in claim 1, wherein L represents a ligand chosen from 1,5-cyclooctadiene and bis (trimethylsilyl)acetylene.

7. A method for the gas-phase chemical deposition of a metal chosen from copper and silver, on a support, wherein said method comprises the step consisting of applying a gas-phase deposition to a copper precursor or silver precursor according to claim 1.

8. The method as claimed in claim 7, wherein the support consists of a material chosen from Si, AsGa, InP, SiC and SiGe.

9. The method as claimed in claim 7, wherein the support contains one or more intermediate layers consisting of at least one material chosen from TiN, TiSiN, Ta, TaN, TaSiN, WN and WSiN.

10. The method as claimed in claim 7, wherein the gas-phase chemical deposition is carried out at a temperature ranging from 120 to 300° C.

11. The method as claimed in claim 7, wherein the copper precursor or silver precursor is used pure.

12. The method as claimed in claim 7, wherein the copper precursor or silver precursor is used in solution in a solvent.

13. A compound as in claim 2, wherein said electron-withdrawing group comprises C1-8 alkenyl.

* * * * *

UNITED STATES PATENT AND TRADEMARK OFFICE
CERTIFICATE OF CORRECTION

PATENT NO. : 7,238,820 B2
APPLICATION NO. : 10/529569
DATED : July 3, 2007
INVENTOR(S) : Doppelt Page 1 of 1

It is certified that error appears in the above-identified patent and that said Letters Patent is hereby corrected as shown below:

Column 9,
Line 67, after the formula, insert the following:
--H(3-NO$_2$-acac)   COD--.

Signed and Sealed this

Thirtieth Day of October, 2007

JON W. DUDAS
*Director of the United States Patent and Trademark Office*